United States Patent
Say et al.

(10) Patent No.: US 10,034,629 B2
(45) Date of Patent: Jul. 31, 2018

(54) SENSOR MODULE WITH ENHANCED CAPILLARY FLOW

(76) Inventors: James L. Say, Breckenridge, CO (US); Stephen L. Pohl, Prescott, WI (US)

( * ) Notice: Subject to any disclaimer, the term of this patent is extended or adjusted under 35 U.S.C. 154(b) by 1194 days.

(21) Appl. No.: 13/978,297

(22) PCT Filed: Jan. 5, 2012

(86) PCT No.: PCT/US2012/020339
§ 371 (c)(1),
(2), (4) Date: Oct. 17, 2013

(87) PCT Pub. No.: WO2012/106060
PCT Pub. Date: Aug. 9, 2012

(65) Prior Publication Data
US 2014/0031654 A1 Jan. 30, 2014

Related U.S. Application Data

(60) Provisional application No. 61/430,384, filed on Jan. 6, 2011.

(51) Int. Cl.
*A61B 5/05* (2006.01)
*A61B 5/157* (2006.01)
(Continued)

(52) U.S. Cl.
CPC ............ *A61B 5/157* (2013.01); *A61B 5/1486* (2013.01); *A61B 5/14532* (2013.01);
(Continued)

(58) Field of Classification Search
CPC .............. A61B 5/1411; A61B 5/14546; A61B 5/150022; A61B 5/150412
See application file for complete search history.

(56) References Cited

U.S. PATENT DOCUMENTS

| | | |
|---|---|---|
| 3,823,035 A | 7/1974 | Sanders |
| 4,255,487 A | 3/1981 | Sanders |

(Continued)

FOREIGN PATENT DOCUMENTS

| | | |
|---|---|---|
| JP | 2007-202632 | 8/2007 |
| WO | WO 2009/148624 A1 | 12/2009 |

(Continued)

OTHER PUBLICATIONS

International Search Report and Written Opinion from International Application No. PCT/US2012/020339 mailed Aug. 27, 2012.
(Continued)

*Primary Examiner* — Puya Agahi
(74) *Attorney, Agent, or Firm* — Merchant & Gould P.C.

(57) ABSTRACT

A sensor module is disclosed herein. The sensor module includes a main housing defining an analysis zone within the housing. The sensor module also includes a skin piercing member mounted within the main housing. The skin piercing member is movable relative to the main housing between a retracted position and an extended position. The main housing of the sensor module defines a fluid sample flow passage that extends from a sampling end of the main housing to the analysis zone. The fluid sample flow passage includes a funnel structure through which the skin piecing member extends when in the extended position. The fluid sample flow passage also includes capillary flow enhancing slots that extend outwardly from opposite sides of the funnel structure.

11 Claims, 13 Drawing Sheets

(51) Int. Cl.
*A61B 5/145* (2006.01)
*A61B 5/1486* (2006.01)
*A61B 5/151* (2006.01)
*A61B 5/15* (2006.01)

(52) U.S. Cl.
CPC ...... *A61B 5/1513* (2013.01); *A61B 5/150022* (2013.01); *A61B 5/15113* (2013.01); *A61B 5/15126* (2013.01); *A61B 5/15142* (2013.01); *A61B 5/15146* (2013.01); *A61B 5/150282* (2013.01); *A61B 5/150412* (2013.01); *A61B 5/1411* (2013.01); *A61B 5/14546* (2013.01); *A61B 5/15105* (2013.01); *A61B 5/150419* (2013.01); *A61B 5/150572* (2013.01)

(56) References Cited

U.S. PATENT DOCUMENTS

| | | | |
|---|---|---|---|
| 4,545,835 A | 10/1985 | Gusack et al. | |
| 4,704,311 A | 11/1987 | Pickering et al. | |
| 5,104,705 A | 4/1992 | Quackenbush | |
| 5,202,261 A | 4/1993 | Musho et al. | |
| 5,262,035 A | 11/1993 | Gregg et al. | |
| 5,264,105 A | 11/1993 | Gregg et al. | |
| 5,320,725 A | 6/1994 | Gregg et al. | |
| 5,356,786 A | 10/1994 | Heller et al. | |
| 5,575,403 A | 11/1996 | Charlton et al. | |
| 5,971,941 A | 10/1999 | Simons et al. | |
| 5,997,501 A | 12/1999 | Gross et al. | |
| 6,099,484 A | 8/2000 | Douglas et al. | |
| 6,143,164 A | 11/2000 | Heller et al. | |
| 6,179,979 B1 | 1/2001 | Hodges et al. | |
| 6,379,317 B1 | 4/2002 | Kintzig et al. | |
| 6,464,849 B1 | 10/2002 | Say et al. | |
| 6,560,471 B1 | 5/2003 | Heller et al. | |
| 6,561,989 B2 | 5/2003 | Whitson | |
| 6,893,545 B2 | 5/2005 | Gotoh et al. | |
| 7,058,437 B2 | 6/2006 | Buse et al. | |
| 7,192,405 B2 | 3/2007 | DeNuzzio et al. | |
| 7,299,081 B2 | 11/2007 | Mace et al. | |
| 7,374,544 B2 | 5/2008 | Freeman et al. | |
| 7,497,997 B2 | 3/2009 | Glezer et al. | |
| 7,604,592 B2 | 10/2009 | Freeman et al. | |
| 7,862,520 B2 | 1/2011 | Briggs et al. | |
| 2001/0041904 A1 | 11/2001 | Heller et al. | |
| 2002/0040208 A1 | 4/2002 | Flaherty et al. | |
| 2002/0130042 A1 | 9/2002 | Moerman et al. | |
| 2003/0153939 A1* | 8/2003 | Fritz | A61B 5/1411 606/181 |
| 2003/0191415 A1 | 10/2003 | Moerman et al. | |
| 2004/0102717 A1 | 5/2004 | Qi | |
| 2004/0236251 A1 | 11/2004 | Roe et al. | |
| 2005/0021066 A1 | 1/2005 | Kuhr et al. | |
| 2005/0067737 A1 | 3/2005 | Rappin et al. | |
| 2006/0241517 A1 | 10/2006 | Fowler et al. | |
| 2007/0149897 A1 | 6/2007 | Ghesquiere et al. | |
| 2007/0170073 A1* | 7/2007 | Wang | A61B 5/14532 205/775 |
| 2008/0167578 A1 | 7/2008 | Bryer et al. | |
| 2008/0243032 A1* | 10/2008 | Hindelang | A61B 5/1411 600/583 |
| 2009/0308184 A1* | 12/2009 | Blekher | A61B 5/1411 73/864.63 |

FOREIGN PATENT DOCUMENTS

| | | |
|---|---|---|
| WO | WO 2010/056869 | 5/2010 |
| WO | WO 2010/056878 | 5/2010 |

OTHER PUBLICATIONS

European Search Report for Application No. 12741872.1 mailed Aug. 21, 2014.

* cited by examiner

FIG. 9  FIG. 10

SENSOR MODULE WITH ENHANCED CAPILLARY FLOW

This application is a National Stage Application of PCT/US2012/020339, filed 5 Jan. 2012, which claims benefit of Ser. No. 61/430,384, filed 6 Jan. 2011 in the USA and which applications are incorporated herein by reference. To the extent appropriate, a claim of priority is made to each of the above disclosed applications.

TECHNICAL FIELD

The present disclosure relates generally sensors. More particularly, the present disclosure relates to sensors for measuring bio-analyte concentrations in blood samples.

BACKGROUND

Electrochemical bio-sensors have been developed for sensing (e.g., detecting or measuring) bio-analyte concentrations in fluid samples. For example, U.S. Pat. Nos. 5,264,105; 5,356,786; 5,262,035; 5,320,725; and 6,464,849, which are hereby incorporated by reference in their entireties, disclose wired enzyme sensors for sensing analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

SUMMARY

One aspect of the present disclosure relates to a wired enzyme sensor module defining an interior sample fluid analysis zone and a sample transport arrangement for consistently, reliably, and relatively quickly transporting a volume of sample fluid (e.g., blood) from a sampling site (e.g., a skin puncture location) to the sample fluid analysis zone. In one embodiment, the sample transport arrangement includes a flow passage configured to enhance capillary flow from the sampling site to the sample fluid analysis zone.

Another aspect of the present disclosure relates to a sample transport arrangement for transporting a blood sample from a sampling site to a sample fluid analysis zone. The sample transport arrangement includes a funnel structure and capillary flow enhancers that project outwardly from opposite sides of the funnel structure. A skin piercing member which passes through the funnel structure is used to create a skin puncture at the sampling site. A volume of blood from the skin puncture is received within the funnel structure. The capillary flow enhancers receive blood from the funnel structure and cause the blood to flow toward the sample fluid analysis zone by capillary action. In one embodiment, the blood from the funnel structure flows at least partially radially outwardly from an axis of the skin piercing member as the blood flows from the funnel structure to the capillary flow enhancers.

A further aspect of the present disclosure relates to a sensor module including a main housing in which a skin piercing member is mounted. The main housing defines a fluid sample analysis zone within the main housing near a sampling end of the main housing. The skin piercing member is movable relative to the main housing along a slide axis between a retracted position where a tip of the skin piercing member is within the main housing and an extended position where the tip of the skin piecing member projects outwardly from the sampling end of the main housing. A wired enzyme sensor arrangement is located at the fluid sample analysis zone. The wired enzyme sensor arrangement includes first and second elongated, generally parallel electrodes. The tip of the skin piecing member moves past the first and second electrodes as the skin piercing member is moved from the retracted position to the extended position. The first and second elongated electrodes are aligned along axes that are offset from the slide axis and that are generally perpendicular with respect to a plane that includes the slide axis.

A further aspect of the present disclosure relates to a sensor module including a main housing in which a skin piercing member is mounted. The main housing defines a fluid sample analysis zone within the main housing near a sampling end of the main housing. The skin piercing member is movable relative to the main housing along a slide axis between a retracted position where a tip of the skin piercing member is within the main housing and an extended position where the tip of the skin piecing member projects outwardly from the sampling end of the main housing. A base of the skin piecing member is anchored to a slide member. The slide member is mounted within a slot defined by the main housing. The slide member moves along the slot as the skin piecing member is moved between the retracted and extended positions.

Still another aspect of the present disclosure relates to a sensor module including a main housing defining a sample fluid analysis zone within the housing. A working electrode is positioned at the sample fluid analysis zone. Sensing chemistry is provided on the working electrode. The sensor module further includes a skin piercing member mounted within the main housing. The skin piercing member is movable between an extended position and a retracted position. The sensor module further includes a sealing member mounted to an exterior of the main housing for sealing the sample fluid analysis zone to increase a shelf-life of the sensing chemistry provided on the working electrode. The shelf-life is extended by limiting the degree to which the sensing chemistry on the working electrode is exposed to air. In one example embodiment, an actuator for moving the skin piercing member between the retracted and extended positions can penetrate the sealing member to access the skin piercing member.

A variety of additional aspects will be set forth within the description that follows. The aspects can relate to individual features and to combinations of features. It is to be understood that both the foregoing general description and the following detailed description are exemplary and explanatory only and are not restrictive of the broad concepts upon which the embodiments disclosed herein are based.

BRIEF DESCRIPTION OF THE DRAWINGS

FIG. 9 is a cross-sectional view taken along section line 9-9 of FIG. 8;

FIG. 10 is a cross-sectional view taken along section line 10-10 of the FIG. 8;

DETAILED DESCRIPTION

Figure 1:
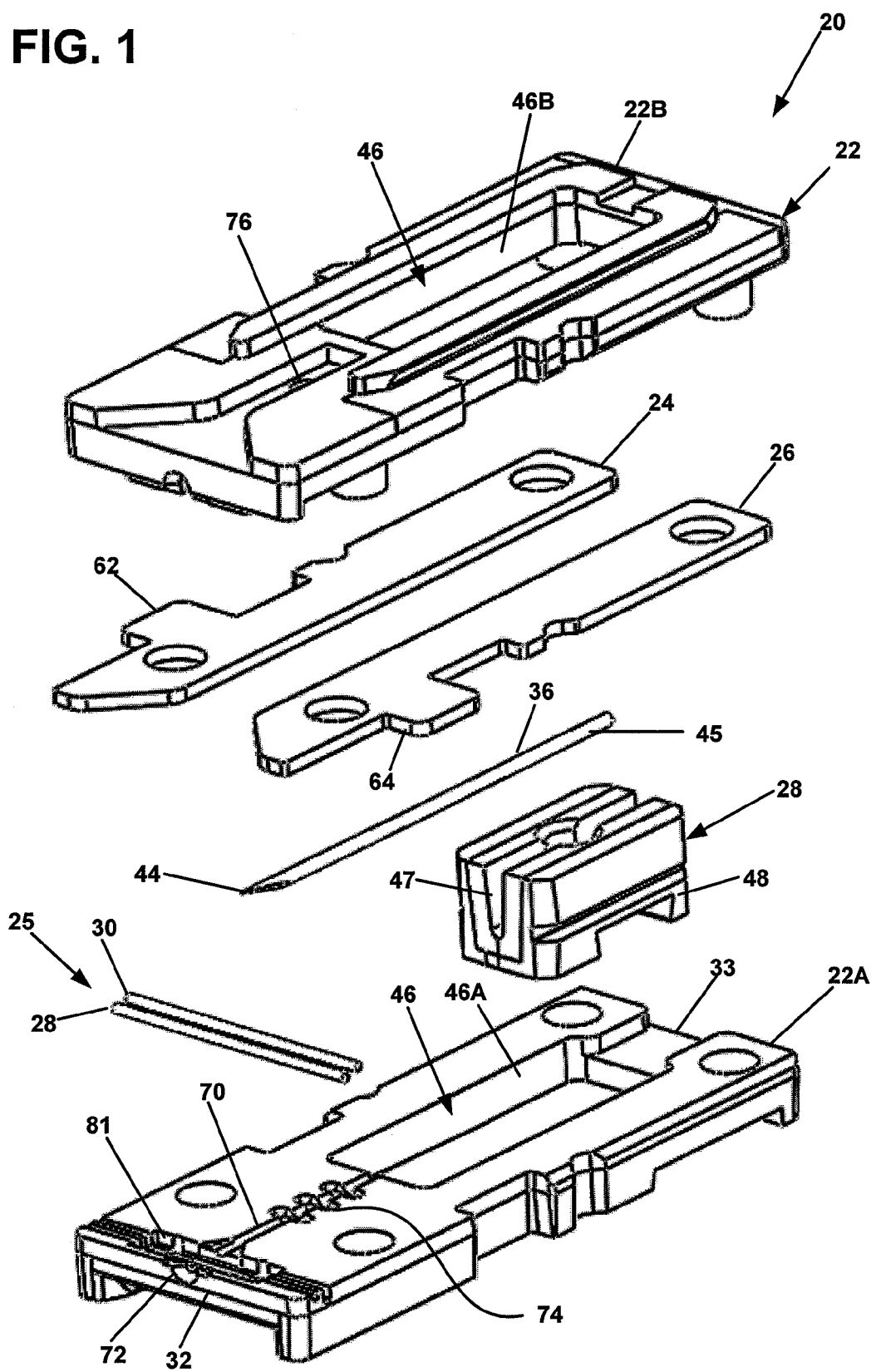
FIG. 1 is an exploded assembly view of a sensor module in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

FIGS. 1-7 illustrate a sensor module 20 in accordance with the principles of the present disclosure. The sensor module 20 includes a main housing 22 in which a skin piercing member 36 is mounted. The skin piercing member 36 is movable relative to the main housing 22 along an axis 40 (see FIG. 3) that extends along a length of the main housing 22. The skin piercing member 36 is movable between a retracted position (see FIG. 3) and an extended position (see FIG. 4). The main housing 22 defines a fluid sample analysis zone 23 (see FIG. 7) within the interior of the main housing 22. The fluid sample analysis zone can also be referred to as a fluid analysis volume, a fluid analysis region, a fluid analysis well, a fluid analysis cell, a fluid analysis site, a fluid analysis location or like terms. An electrode arrangement 25 (e.g., a wired enzyme sensing arrangement) is positioned within the main housing 22 at the sample analysis zone 23. The main housing 22 further includes a sampling end 32 at which a sample fluid access structure 27 is located. The sample fluid access structure 27 includes a flow transport arrangement in the form of a flow passage 42 that extends from the sampling end 32 of the main housing 22 to the sample analysis zone 23. The flow passage 42 is configured to enhance capillary flow of a fluid sample (e.g., blood) from the sampling end 32 of the main housing 22 to the sample analysis zone 23. For example, the flow passage 42 includes a central funnel structure 72 through which the skin piercing member 36 passes as it is moved from the retracted position to the extended position. The funnel structure 72 provides a volume or reservoir for collecting blood received from a skin puncture site caused by the skin piercing member 36. The flow passage 42 further includes capillary flow enhancers 90 in fluid communication with the reservoir formed by the funnel structure 72. The capillary flow enhancers 90 project outwardly from opposite sides of the funnel structure 72. The capillary flow enhancers 90 provide increased surface area for drawing blood outwardly from the funnel structure 72 via capillary action and for causing said blood to move by capillary action from the sampling end 32 of the main housing 22 to the sample analysis zone 23.

In use of the sensor module 20, the sampling end 32 of the main housing 22 is placed against a patient's skin at a sampling site where it is desired to take a fluid (e.g., blood) sample. Once the sampling end 32 is in contact with the skin, the skin piercing member 36 is moved from the retracted position to the extended position thereby causing a tip of the skin piercing member 36 to pierce the patient's skin and generate a blood sampling site. The skin piercing member 36 is then moved from the extended position back to the retracted position. Upon retraction of the skin piercing member 36, blood from the blood sampling site fills the reservoir formed by the funnel structure 72. The blood within the funnel structure 72 is caused at least in part by capillary action to move from the sampling end 32 of the main housing 22 toward the sample analysis zone 23. The capillary flow enhancers 90 enhance capillary flow from the funnel structure 72 to the sample analysis zone 23. In this way, blood is relatively quickly and uniformly provided to the analysis zone 23. As shown by the flow arrows at FIG. 7, the capillary flow enhancers 90 cause blood to flow via capillary action outwardly from the funnel structure 72 at least partially in a radial direction relative to the axis 40. The capillary flow enhancers 90 also cause blood to move by capillary action in a direction toward the sample analysis zone 23. At the sample analysis zone 23, an analyte level (e.g., blood glucose level) in the blood sample is sensed through the use of a wired enzyme sensor arrangement including the electrode arrangement 25. It will be appreciated that the electrode arrangement can be operatively connected to a sensor control system.

Figure 2:
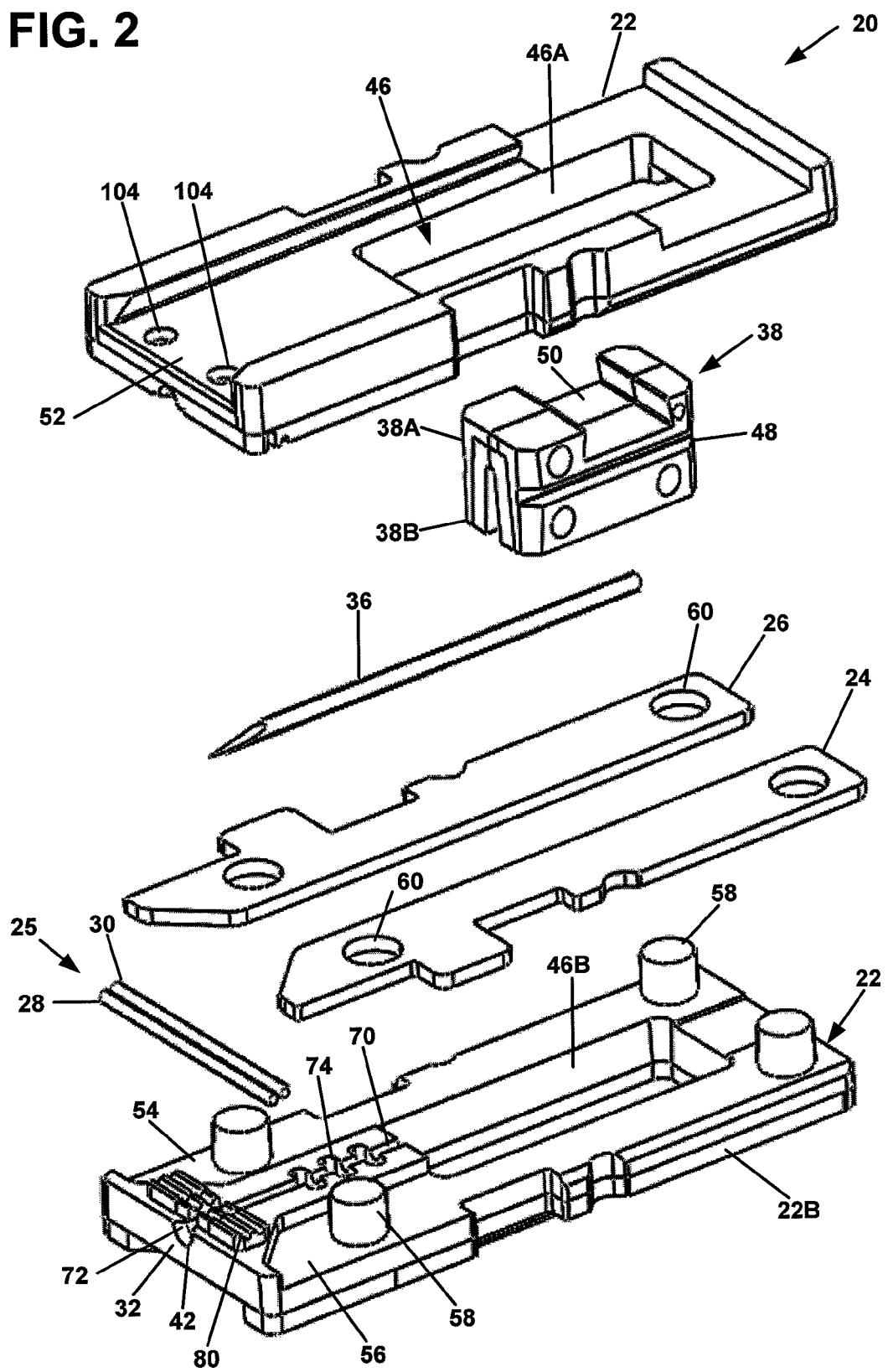
FIG. 2 is another exploded assembly view of the sensor module of FIG. 1 showing opposite sides of the various components of the assembly.
Figure 3:
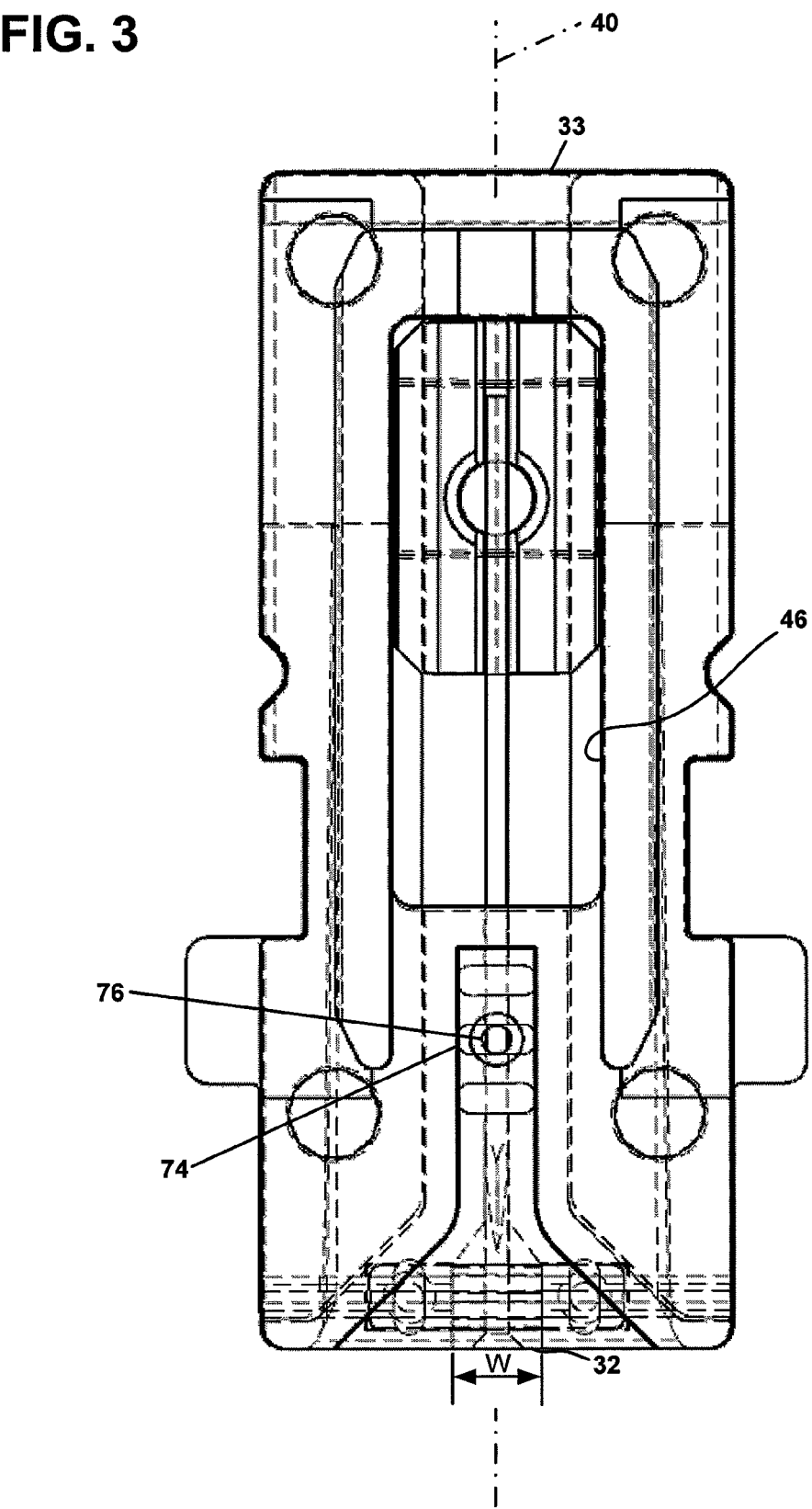
FIG. 3 is a plan view of the sensor module of FIG. 1 with a skin piercing member of the sensor module in a retracted position.
Figure 4:
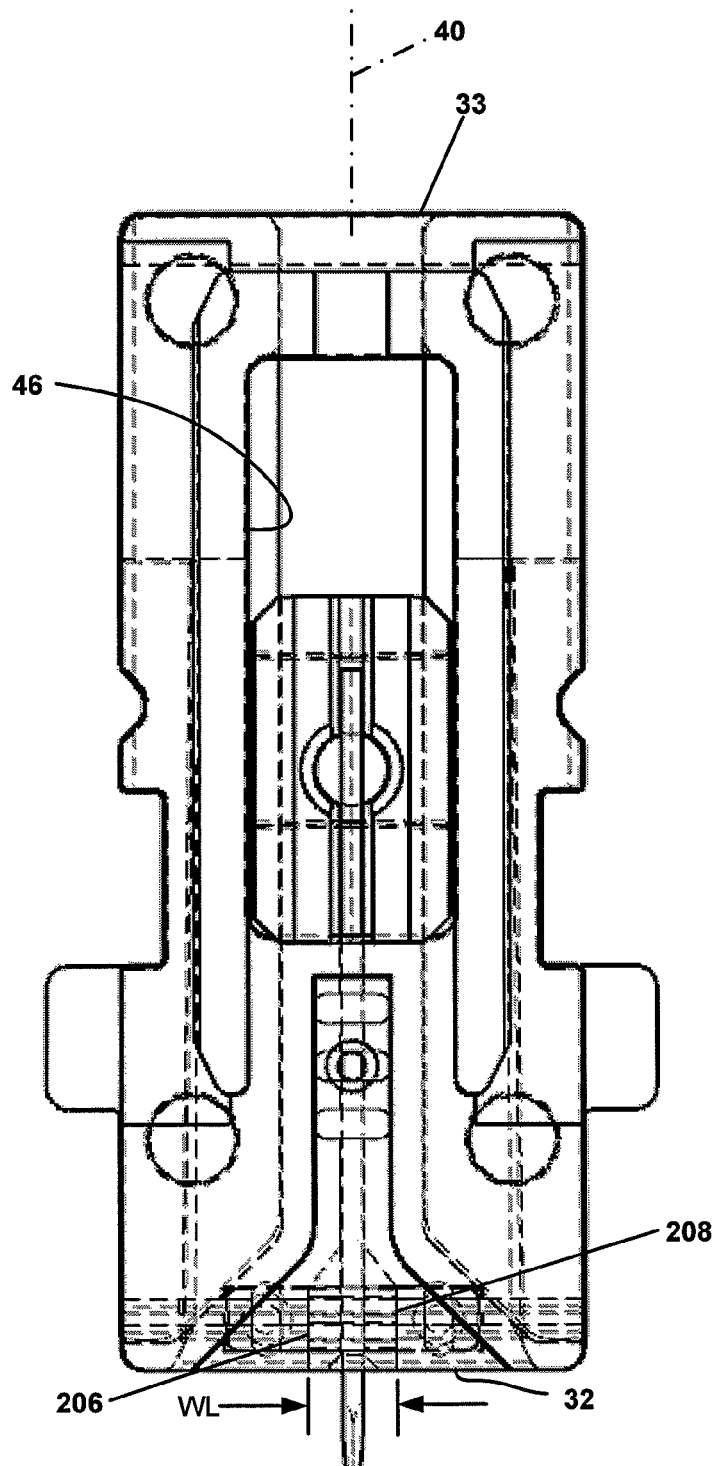
FIG. 4 is a plan view of the sensor module of FIG. 1 with the skin piercing member in an extended position.

Referring to FIGS. 1 and 2, the main housing of the sensor module 20 includes a first piece 22A and a second piece 22B. The sensor module 20 also includes two electrical contacts 24, 26 that mount between the first and second pieces 22A, 22B of the main housing 22. The electrode arrangement 25 of the sensor module 20 includes two electrodes 28, 30 mounted between the first and second pieces 22A, 22B of the main housing 22 at a location near a sampling end 32 of the sensor module 20. One of the electrodes 28, 30 is preferably a working electrode while the other of the electrodes 28, 30 is preferably a counter electrode or a counter/reference electrode. One of the electrodes 28, 30 is electrically connected to the electrical contact 24 and electrically isolated from the electrical contact 26, while the other of the electrodes 28, 30 is electrically connected to the electrical contact 26 and is electrically isolated from the electrical contact 24. The contacts 24, 26 respectively have contact tabs 62, 64 for facilitating electrically connecting the contacts to a sensor control system.

The skin piercing member 36 of the sensor module 20 includes a sharp tip 44 and a base 45. The base 45 is anchored within a notch 47 defined by a slide member 38. The skin piecing member 36 and the slide member 38 together form a skin piercing assembly. The skin piercing member 36 can be a cannula, needle, lancet or other similar structure.

Referring back to FIG. 1, the main housing 22 of the sensor module is relatively compact. For example, in one non-limiting embodiment, the main housing 22 is generally rectangular in shape and has a length that is less than 1 inch. The main housing includes opposite major sides and opposite minor sides that extend along the length of the main housing 22 between opposite ends (e.g., the sampling end 32 and non-sampling end 33) of the main housing. The main housing 22 defines an elongated slot 46 for receiving and guiding movement of the slide member 38 to which the skin piercing member 36 is anchored. The slot 46 is elongated along the axis 40 and includes a first portion 46A defined by the first piece 22A of the main housing 22 and a second portion 46B defined by the second piece 22B of the main housing 22. The first portion 46A of the slot 46 receives a first portion 38A of the slide member 38 and the second portion 46B of the slot 46 receives a second portion 38B of the slide member 38. Rails 48 of the slide member 38 are captured between the first and second pieces 22A, 22B to limit upward or downward movement of the slide member 38 relative to the main housing 22. The first portion 38A of the slide member 38 defines a notch 50 for use in mechanically coupling an actuator to the slide member 38. The actuator can be incorporated into an analyte monitoring unit having a cartridge for holding a plurality of the sensor modules, and can be used to move the skin piercing assembly between the retracted and extended positions. The first piece 22A of the main housing 22 also includes a groove 52 positioned at one of the major sides of the main housing 22. The groove 52 can be adapted for receiving a dove-tailed shaped tongue for mounting the sensor module 20 to the analyte monitoring unit.

Referring again to FIG. 1, the electrical contacts 24, 26 are mounted within recesses 54, 56 defined by the second piece 22B of the main housing 22. The second piece 22B also includes posts 58 that are received within openings 60 of the electrical contacts 24, 26 to position the contacts 24, 26 within the main housing 22 and to limit movement of the electrical contacts 24, 26 relative to the main housing 22. The electrical contact tabs 62, 64 of the contacts 24, 26 are configured to project outwardly from the opposite minor sides of the main housing 22. In a preferred embodiment, the electrical contacts 24, 26 are made of an electrically conductive material such as metal.

The first and second pieces 22A, 22B of the main housing 22 cooperate to define a skin piercing member passage 70 aligned along the axis 40. It will be appreciated that the axis 40 is coaxially aligned with the skin piercing member 36 and the skin piercing member passage 70. The skin piercing member passage 70 extends from the slot 46 to the sampling end 32 of the main housing 22. At the sampling end 32, the skin piercing member passage 70 expands outwardly to form the funnel structure 72. The funnel structure 72 has a major cross-dimension CD1 (e.g., a major diameter) at the sampling end 32 of the main housing 22 and a minor cross-dimension CD2 (e.g., a minor diameter) inwardly offset from the sampling end 32 of the main housing 22. Thus, the funnel structure 72 tapers radially outwardly away from the axis 40 as the funnel structure 72 extends away from the fluid analysis zone 23 and toward the sampling end 32. In the depicted embodiment, the funnel structure 72 has a truncated conical shape. In other embodiments, other tapered shapes (e.g., a truncated pyramid shape) could be used.

To prevent blood flow from passing through the skin piercing member passage 70 to the slot 46, a plurality of wells 74 are provided in fluid communication with the skin piercing member passage 70. The wells 74 preferably each have a large enough volume to prevent blood flow via capillary action from reaching the slot 46. In other embodiments, a sealant can be injected into one or more of the wells 74 via a port 76 such that the sealant forms a seal about the skin piercing member 36 which allows the skin piercing member 36 to slide within the skin piercing member passage 70 between the extended and retracted positions while concurrently preventing blood flow from flowing through the skin piercing member passage 70 to the slot 46.

Figure 9A:
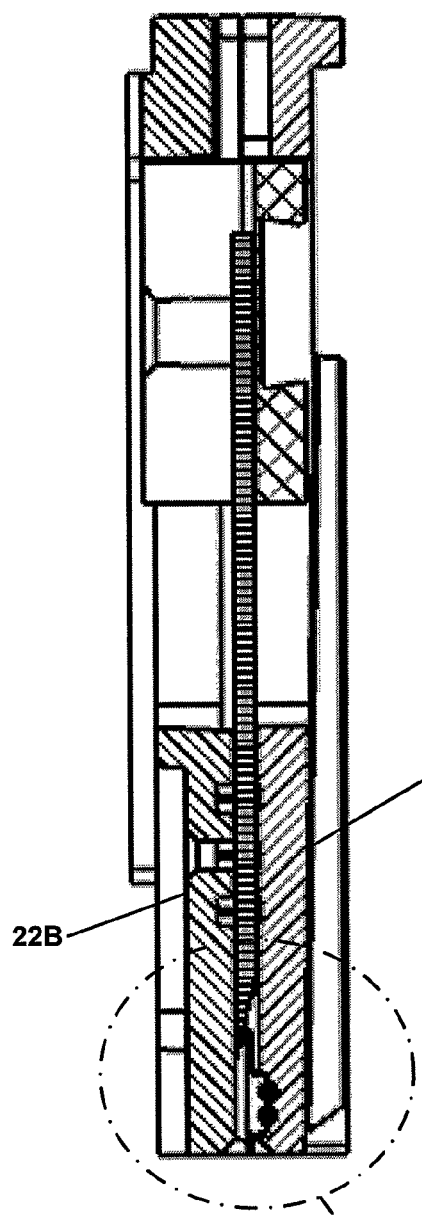
FIG. 9A is an enlarged view of a portion of FIG. 9.
Figure 10A:
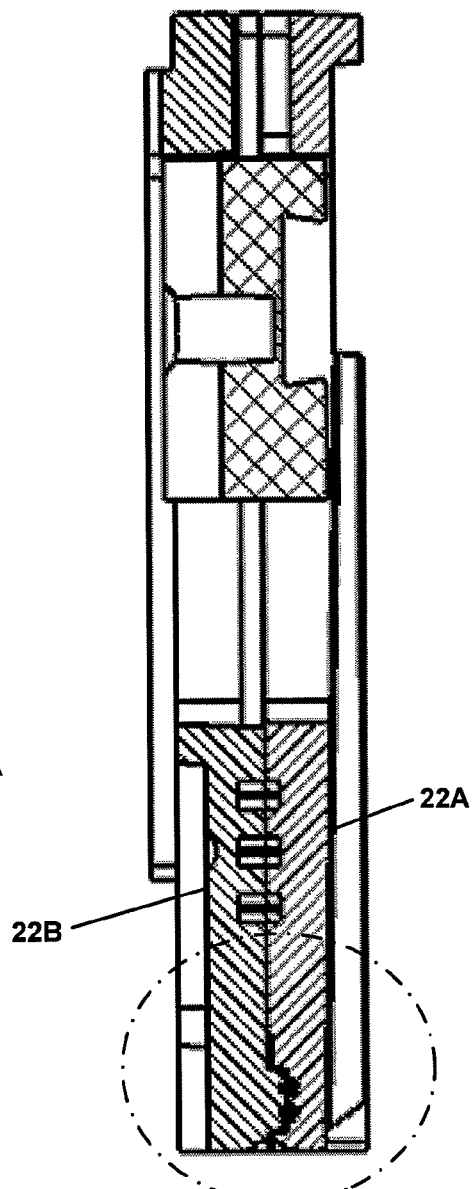
FIG. 10A is an enlarged view of a portion of FIG. 10.
Figure 9A:
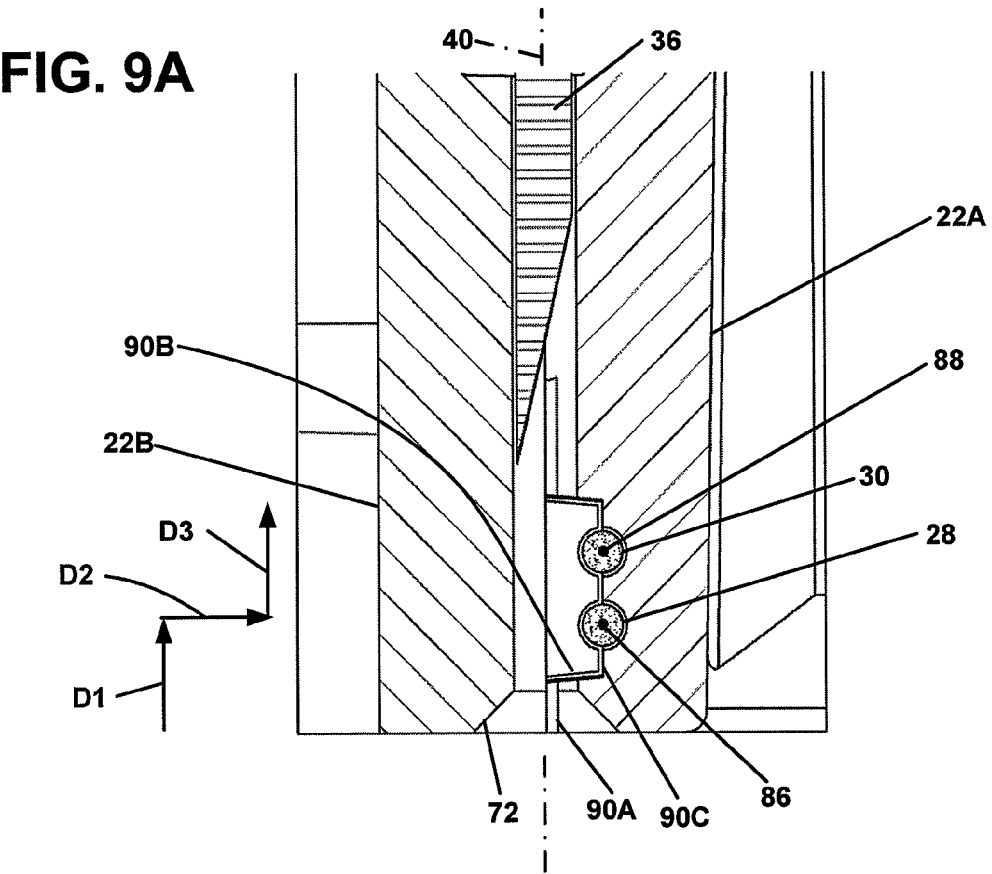
Figure 10A:
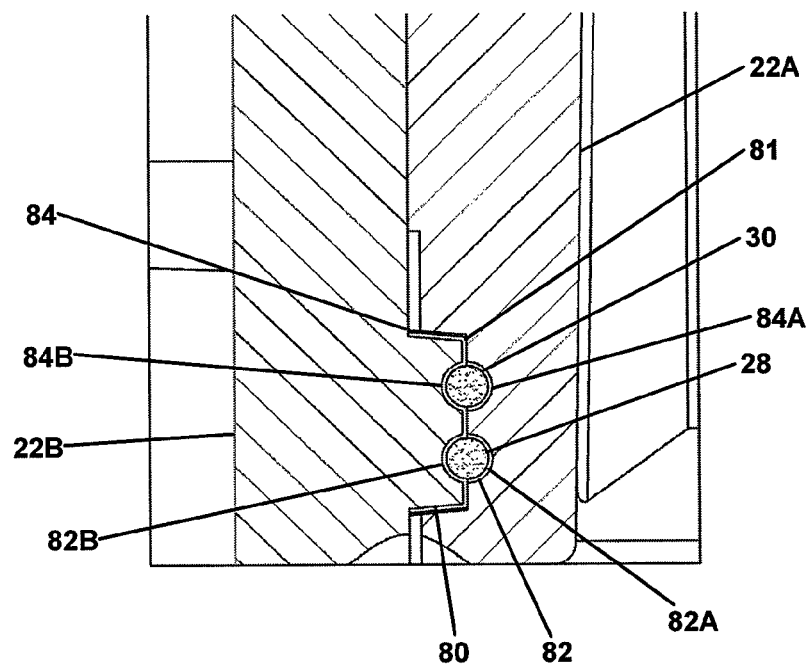
Figure 11:
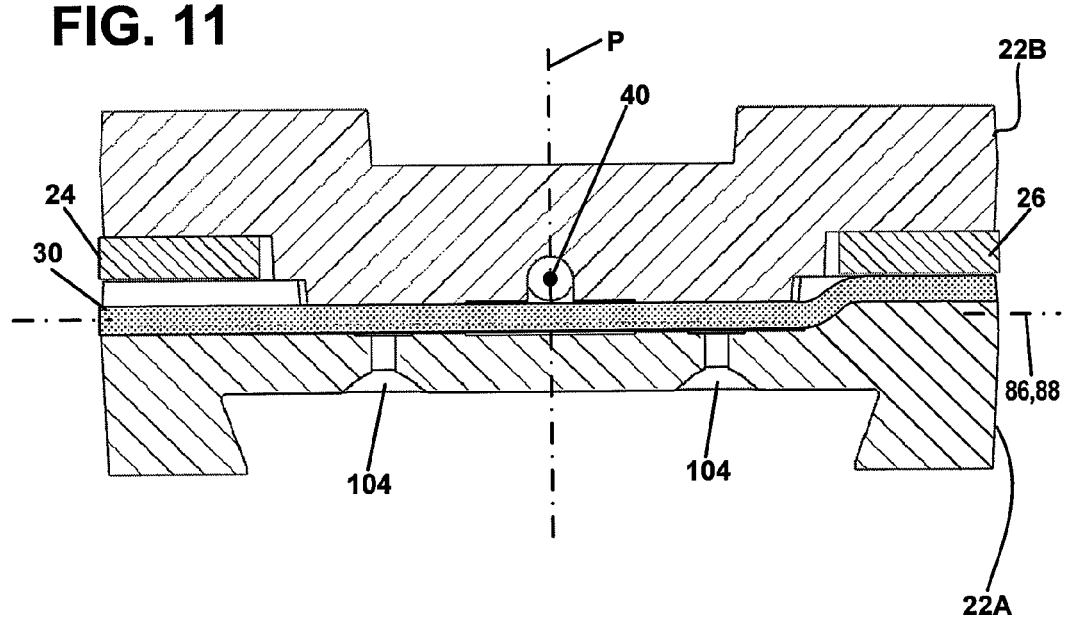
FIG. 11 is a cross-sectional view taken along section line 11-11 of FIG. 8.
Figure 12:
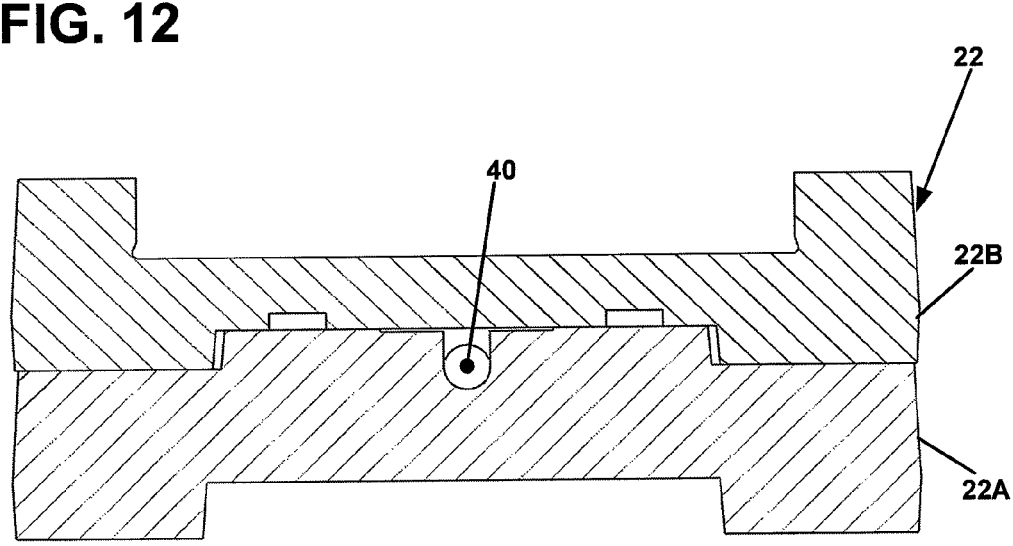
FIG. 12 is a cross-sectional view taken along section line 12-12 of FIG. 8.

Referring again to FIGS. 1 and 2, the second piece 22B includes an electrode offset mount 80 configured to offset the electrodes 28, 30 from the skin piercing member passage 70. As depicted in FIG. 2, the offset mount 80 projects upwardly from a main body of the second piece 22b and fits within a pocket 81 (see FIG. 1) defined by the first piece 22A. The offset mount 80 defines generally parallel grooves 82B, 84B that are offset from the skin piercing member passage 70 (see FIG. 9A). The grooves 82B, 84B cooperate with grooves 82A, 84A defined within the pocket 81 of the first piece 22A to define passages 82, 84 that respectively receive the electrodes 28, 30. The electrodes 28, 30 define axes 86, 88 that are transverse relative to a plane P (see FIG. 11) including the slide axis 40. When the electrodes 28, 30 are mounted at the offset mount 80, the axes 86, 88 are offset from the slide axis 40 (see FIG. 11). In the depicted embodiment, the axes 86, 88 are generally perpendicular relative to the plane P (see FIG. 11) including the slide axis 40.

As used herein, generally perpendicular means perpendicular or almost perpendicular. As used herein, generally parallel means parallel or almost parallel. As used herein, transverse means extending across.

Figure 5:
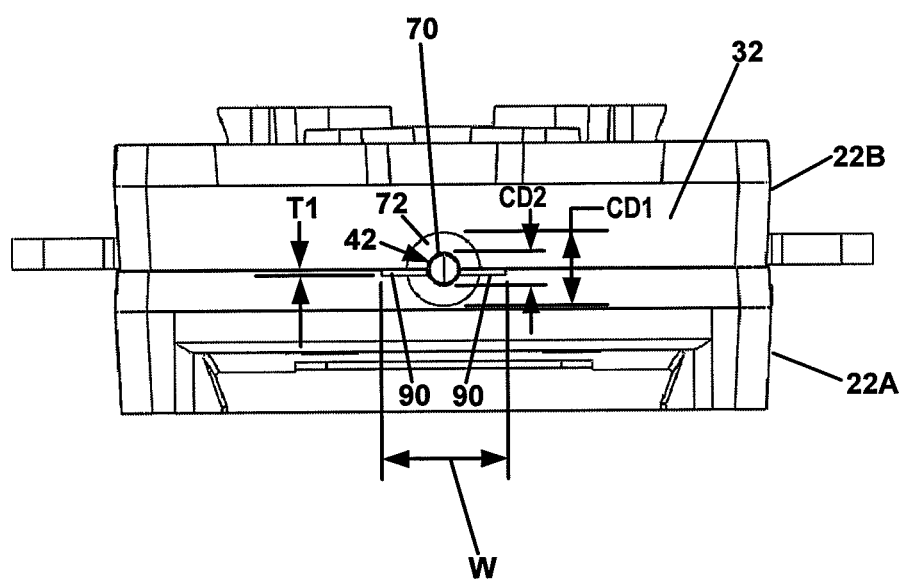
FIG. 5 is an end view of the sensor module of FIG. 1 showing a sampling end of the sensor module.
Figure 6:
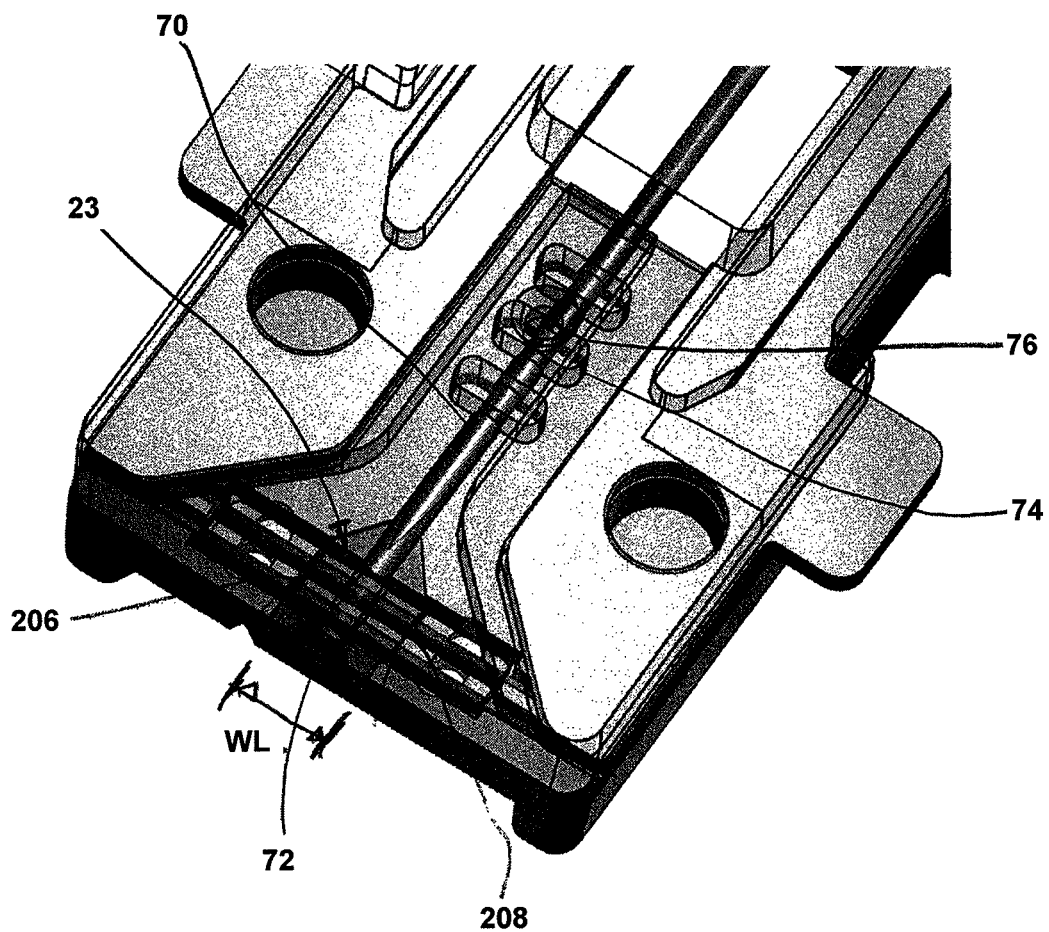
FIG. 6 is a perspective view showing the sampling end of the sensor module of FIG. 1.
Figure 7:
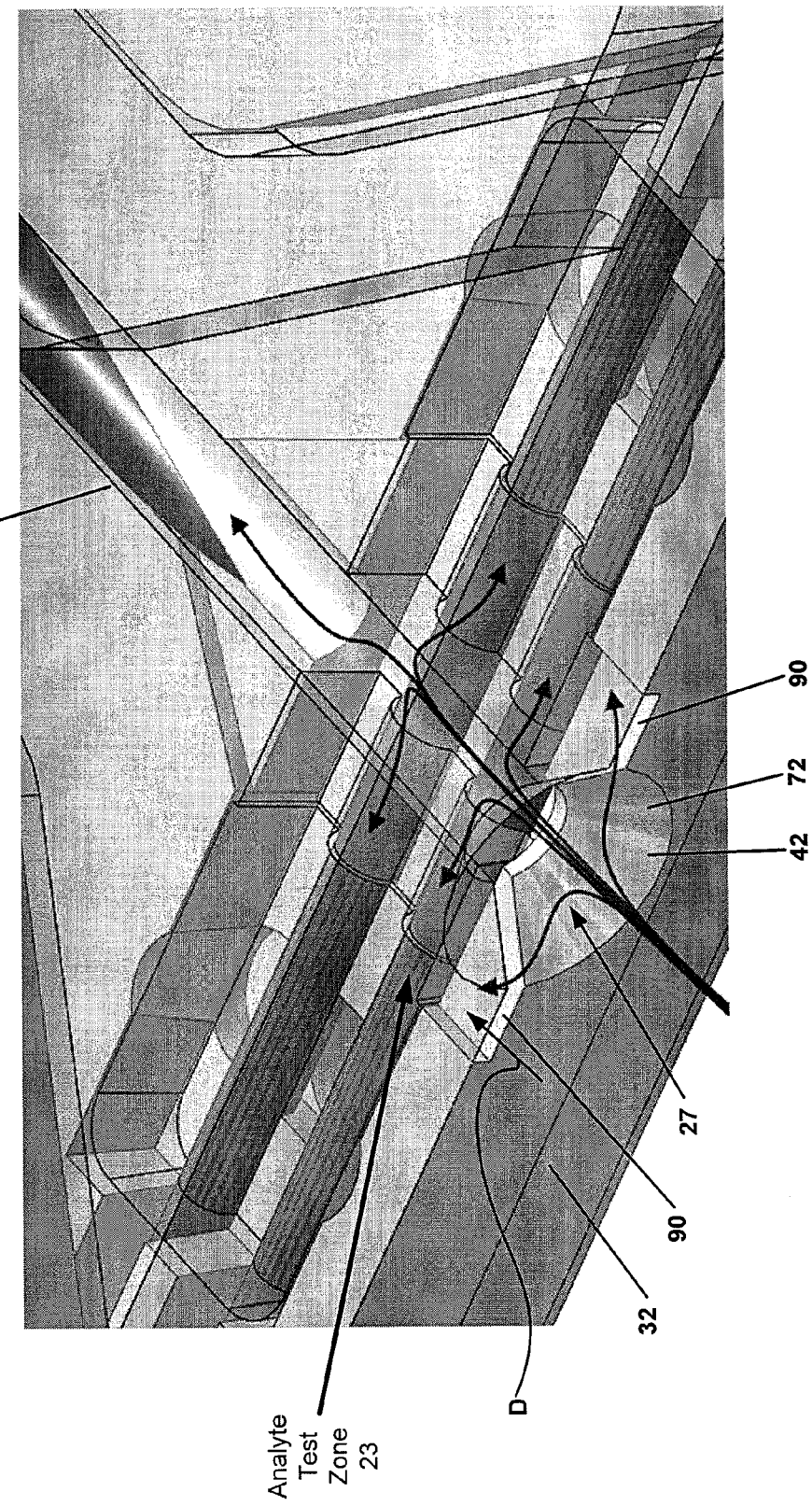
FIG. 7 is a perspective view showing a sample fluid transport arrangement of the sensor module of FIG. 1, the sample fluid transport arrangement is adapted for transporting a sample fluid (flow shown by arrows) from the sampling end of the sensor module to a sample fluid analysis zone.
Figure 8:
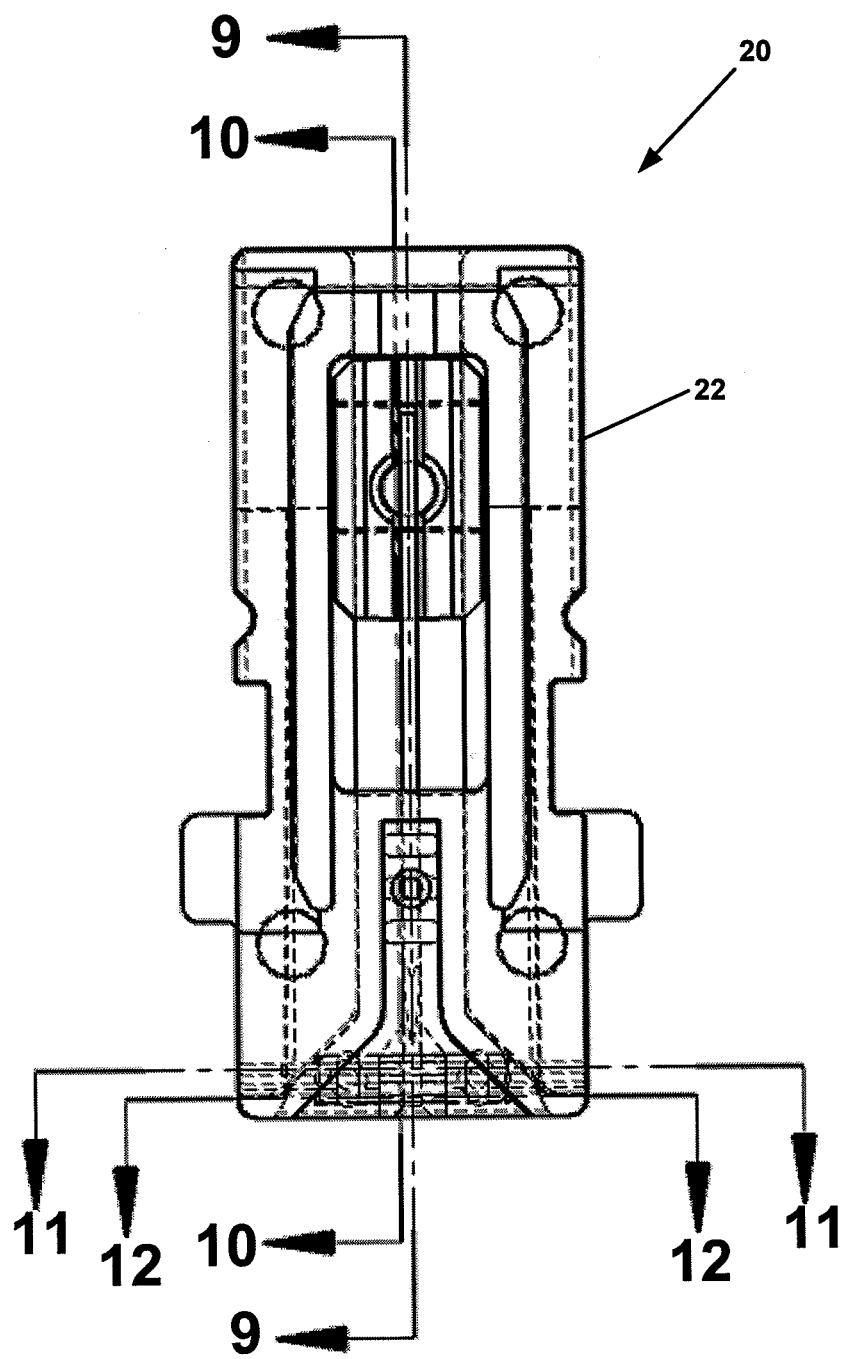
FIG. 8 is a plan view of the sensor module of FIG. 1 with various cross-section lines depicted.

Referring to FIGS. 6, 7, 9A and 10A, the sample fluid analysis zone 23 is formed by a volume of open space including at least portions that circumferentially surround portions of the electrodes 28, 30. During a sampling and analysis operation, blood flows through the flow passage 42 and fills the volume provided at the sample fluid analysis zone 23. As shown at FIGS. 5 and 7, the funnel structure 72 of the flow passage 42 is centered on the slide axis 40. The capillary flow enhancers 90 of the flow passage 42 are positioned on opposite sides of the funnel structure 72. The capillary flow enhancers 90 are in fluid communication with the funnel structure 72 and are configured to project outwardly from the funnel structure 72 to increase an overall width W of the flow passage 42. As depicted at FIG. 5, the capillary flow enhancers 90 project outwardly from the funnel structure 72 in opposite outward radial directions relative to the axis 40. In one embodiment, the overall width W of the flow passage is in the range of 0.04 to 0.08 inches. In another embodiment, the overall width W is in the range of 0.05 to 0.07 inches. In still another embodiment, the overall width W is about 0.060 inches. In certain embodiments, the overall width W is at least 3 times greater than the cross-dimension CD2 of the skin piercing member passage 70. In certain embodiments, the capillary flow enhancers 90 increase the overall width W by at least 30 percent as compared to the major cross-dimension CD1 of the funnel structure 72. The width W is measured in a direction generally perpendicular to a primary flow direction D from the sampling end 32 of the housing 22 to the sample fluid analysis zone 23. In certain embodiments, the overall width W is at least 50 percent, or at least 75 percent, or at least 90 percent, or about 100 percent as long as a wetted length WL of either of the electrodes 28, 30. The wetted length WL is the length of each of the electrodes 28, 30 that is exposed to a fluid sample during analysis of the fluid sample.

The capillary flow enhancers 90 are shown as slots defined between generally parallel, planar surfaces separated by a thickness T1. The thickness T1 is selected to promote capillary flow through the capillary flow enhancers 90. In certain embodiments, thickness T1 is in the range of 0.002 to 0.004 inches. In other embodiments, the thickness T1 is less than or equal to 0.004 inches. In still other embodiments, the thickness T1 is about 0.003 inches. In certain embodiments, the opposing surfaces separated by the thickness T1 can be textured as disclosed at U.S. Pat. No. 5,104,705, which is hereby incorporated by reference, so as to further enhance capillary flow between the surfaces. In other embodiments, the opposing surfaces are not textured. In certain embodiments, the volume of open space circumferentially surrounding the electrodes 28, 30 is equal to about one-half the thickness T1.

The capillary flow enhancers 90 also include dimensions D1 that extend into the main housing 22 in a direction generally parallel to the slide axis 40. Inner open regions of the capillary flow enhancers 90 are contiguous with the funnel structure 72 and angle inwardly toward the slide axis 40 as the edges defined between the funnel structure 72 and the flow enhancers 90 extend into the main housing 22.

The capillary flow enhancers 90 include first portions 90A that extend along the dimension D1 that is parallel to the axis 40. The capillary flow enhancers 90 also include second portions 90B in fluid communication with the first portions 90A. The second portions 90B extend in a direction D2 generally perpendicular with respect to the direction D1 such that flow is stepped toward the electrodes 28, 30 to account for the offset between the axis 40 and the axes 86, 88 of the electrodes 28, 30. The capillary flow enhancers 90 further include third portions 90C in fluid communication with the second portions 90B. The third portions 90C extend from the second portions 90B to the volume corresponding to the analysis zone 23. The third portions 90C extend in a direction D3 that is generally parallel to the direction D1.

In certain embodiments, opposite ends of the analysis zone 23 can be sealed adjacent the electrodes 28, 30 by laser welds provided between the first and second pieces 22A, 22B of the main housing 22. In certain embodiments, the second piece 22B can be transparent and the first piece 22A can be opaque such that a laser can be directed through the second piece 22B to provide a laser weld at the interface between the pieces 22A, 22B along lines 206, 208 (see FIG. 6) that traverse the electrodes 28, 30. A mask can be used to protect the chemistry/reactive enzymes provided on the electrodes 28, 30 within the analysis zone 23 (e.g., between the boundary lines 206, 208). The laser can be used to ablate chemistry that is not covered by the mask. In this way, a laser can be used to concurrently provide a seal about a portion of the analysis zone 23 and to ablate excess sensor chemistry. If laser welding does not provide suitable seals about the electrodes 28, 30, a sealant can be injected through ports 104 to assist in sealing the analysis zone 23 along the lines 206, 208 traversing the electrodes 28, 30.

In use of the sensor module 20, the sampling end 32 is pressed against a person's skin and the skin piercing member 36 is used to create a sampling site in the form of a puncture wound. Blood from the wound site enters the funnel structure 72 and flows into the capillary flow enhancers 90 by capillary action. Flow within the first portions of 90A of the capillary flow enhancers 90 moves both along the dimension D1 and also radially outwardly from the axis 40. Flow within the second portions 90B of the capillary flow enhancers 90B moves along the dimension D2. Capillary flow along the third portions 90C moves along the dimension D3 to the volume corresponding to the analysis zone 23. The third portions 90C of the capillary flow enhancers 90 meet with the analysis zone generally at a plane that includes the axes 86, 88 of the electrodes 28, 30. Flow from the third portions 90C of the capillary flow enhancers travels above and below the electrodes 28, 30 via capillary action such that the electrodes are circumferentially surrounded by blood. Additional flow can also enter the analysis zone 23 through the skin piercing member passage 70. Such flow can move into the analysis zone 23 by flowing from the skin piercing member passage 70 outwardly along the outer surfaces of the electrodes 28, 39 in directions that extend along the axes 86, 88 of the electrodes 28, 30.

In one embodiment, the electrode 28 is in contact with a sensing layer and functions as a working electrode and the electrode 30 can function as a reference/counter electrode. In other embodiments, separate working, reference and counter electrodes can be provided in fluid communication with the analysis zone 23. The electrodes 28, 30 are preferably threads, fibers, wires, or other elongated members.

In one embodiment, the working electrode can include an elongated member that is coated or otherwise covered with a sensing layer and the reference/counter electrode can include any elongated member, such as a wire or fiber that is coated or otherwise covered with a layer, such as silver chloride. Preferably, at least a portion of each elongated member is electrically conductive. In certain embodiments, each elongated member can include a metal wire or a glassy carbon fiber. In still other embodiments, each elongated member can each have a composite structure and can include a fiber having a dielectric core surrounded by a conductive layer suitable for forming an electrode.

A preferred composite fiber is sold under the name Resistat® by Shakespeare Conductive Fibers LLC. This composite fiber includes a composite nylon, monofilament, conductive thread material made conductive by the suffusion of about a 1 micron layer of carbonized nylon isomer onto a dielectric nylon core material. The Resistat® material is comprised of isomers of nylon to create the basic 2 layer composite thread. However, many other polymers are available for the construction, such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrolle can be incorporated into the conductive layer along with the carbon to complete the formulation. In certain embodiments, the ICP can be used as the electrode surface alone or in conjunction with carbon. The Resistat® fiber is availability in diameters of 0.0025 to 0.016 inches, which is suitable for sensor electrodes configured in accordance with the principles of the present disclosure. Example patents disclosing composite fibers suitable for use in practicing sensor modules configured in accordance with the principles of the present disclosure include U.S. Pat. Nos. 3,823,035; 4,255,487; 4,545,835 and 4,704,311, which are hereby incorporated herein by reference in their entireties.

The sensing layers provided at working electrodes of sensor modules configured in accordance with the principles of the present disclosure can include a sensing chemistry, such as a redox compound or mediator. The term redox compound is used herein to mean a compound that can be oxidized or reduced. Example redox compounds include transition metal complexes with organic ligands. Preferred redox compounds/mediators include osmium transition metal complexes with one or more ligands having a nitrogen containing heterocycle such as 2,2'-bipyridine. The sensing material also can include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In sensor systems, such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

During sample analysis at the analysis zone 23, a voltage can be applied between the electrodes 28, 30. When the potential is applied, an electrical current will flow through the fluid sample between the electrodes 28, 30. The current is a result of the oxidation or reduction of an analyte, such as glucose, in the volume of fluid sample located within the analysis zone. This electrochemical reaction occurs via the electron transfer agent in the sensing layer and an optional electron transfer catalyst/enzyme in the sensing layer. By measuring the current flow generated at a given potential (e.g., with a controller described herein), the concentration of a given analyte (e.g., glucose) in the fluid sample can be determined. Those skilled in the art will recognize that current measurements can be obtained by a variety of techniques including, among other things, coulometric, potentiometric, perometric, voltometric, and other electrochemical techniques.

Figure 13:
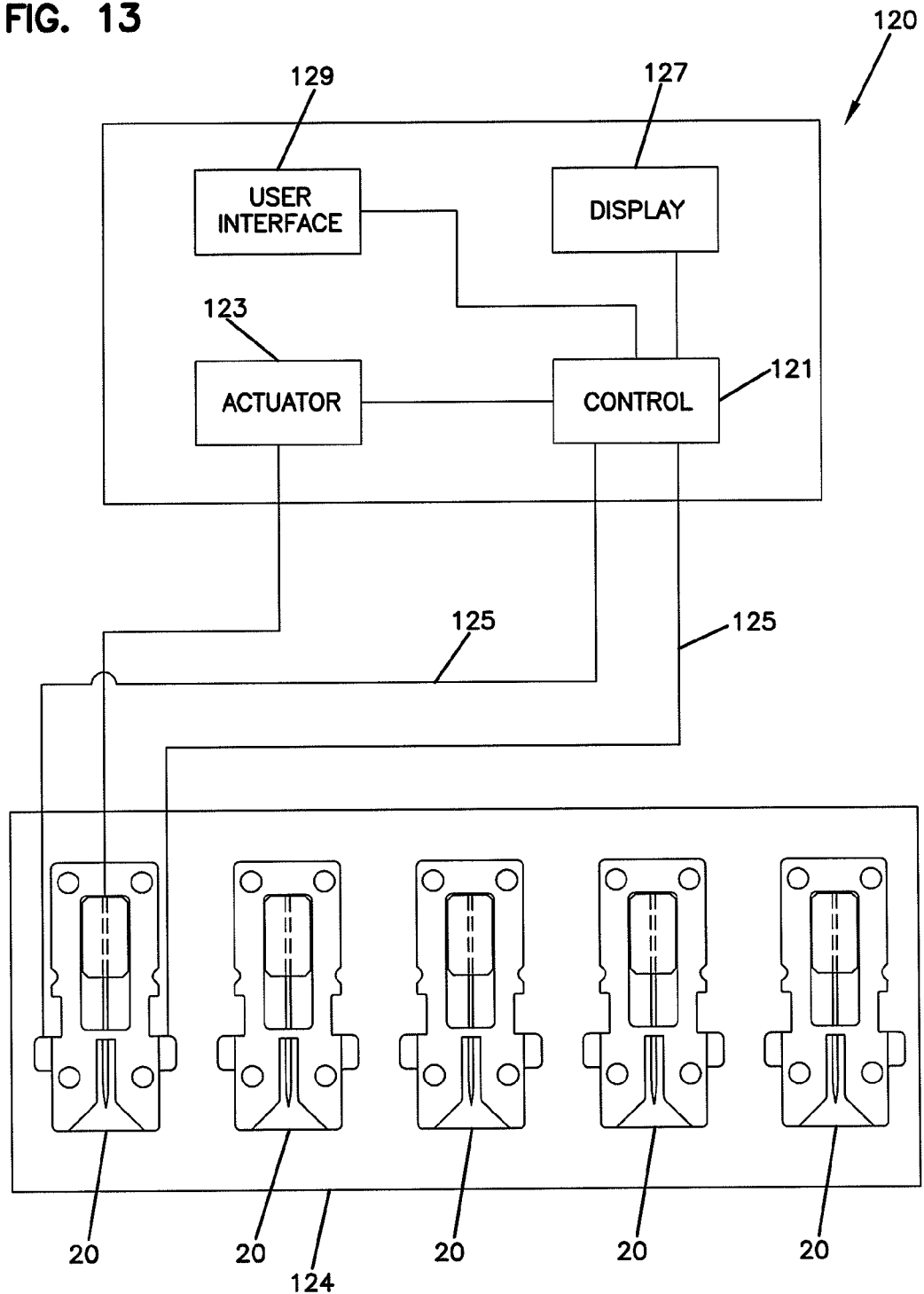
FIG. 13 is a schematic view of a sensing unit in accordance with the principles of the present disclosure that incorporates a plurality of the sensing modules of FIG. 1.

Referring to FIG. 13, it will be appreciated that one or more sensor modules 20 can be incorporated as sub-components into an analyte monitoring unit 120. The unit 120 includes a controller 121 that couples to a module holder 124. The module holder 124 is configured to hold one or more sensor modules 20. Each sensor module 20 is configured to obtain one or more fluid samples, to measure a concentration level for one or more analytes (e.g., glucose, lactate, etc.), and to generate a signal (e.g., an electrical signal) indicating the concentration level. For example, the module holder 124 shown in FIG. 13 contains five sensor modules 20. In one embodiment, each sensor module 20 is configured to analyze a single fluid sample. In such an embodiment, the sensor module 20 can be removed from the module holder 124 after one use. In other embodiments, each sensor module 20 can be configured to analyze a greater number of fluid samples.

In general, the unit 120 includes a controller 121, an actuator 123, and input lines 125. The controller 121 controls the actuator arrangement 123 for driving the skin piercing members 36 of each sensor module 20 between the extended and retracted positions to obtain a fluid sample. The controller 121 can include a microcontroller, a mechanical controller, software driven controller, a hardware driven controller, a firmware driven controller, etc. The controller can include a microprocessor that interfaces with memory.

The controller 121 instructs the actuator arrangement 123 when to operate the sensor module 20 to obtain a fluid sample for analysis. The controller 121 also can instruct the module holder 124 and/or the actuator arrangement 123 to eject the used sensor module 20.

The input lines 125 carry the data/signals/readings (e.g., voltage values) generated at the electrodes 28, 30 of the sensor module 20 during analysis of a fluid sample to the controller 121 for analysis. The controller 121 converts the signals to an analyte concentration level (e.g., a blood glucose reading) or other desired information. The controller 121 causes the display 127 to indicate the processed information to the user. Other information also can be presented on the display 127. In one embodiment, the display 127 is a visual display. In other embodiments, an audio display also can be used. Additional information can be provided to the processor 121 via a user interface 129 (e.g., buttons, switches, etc.).

Figure 14:
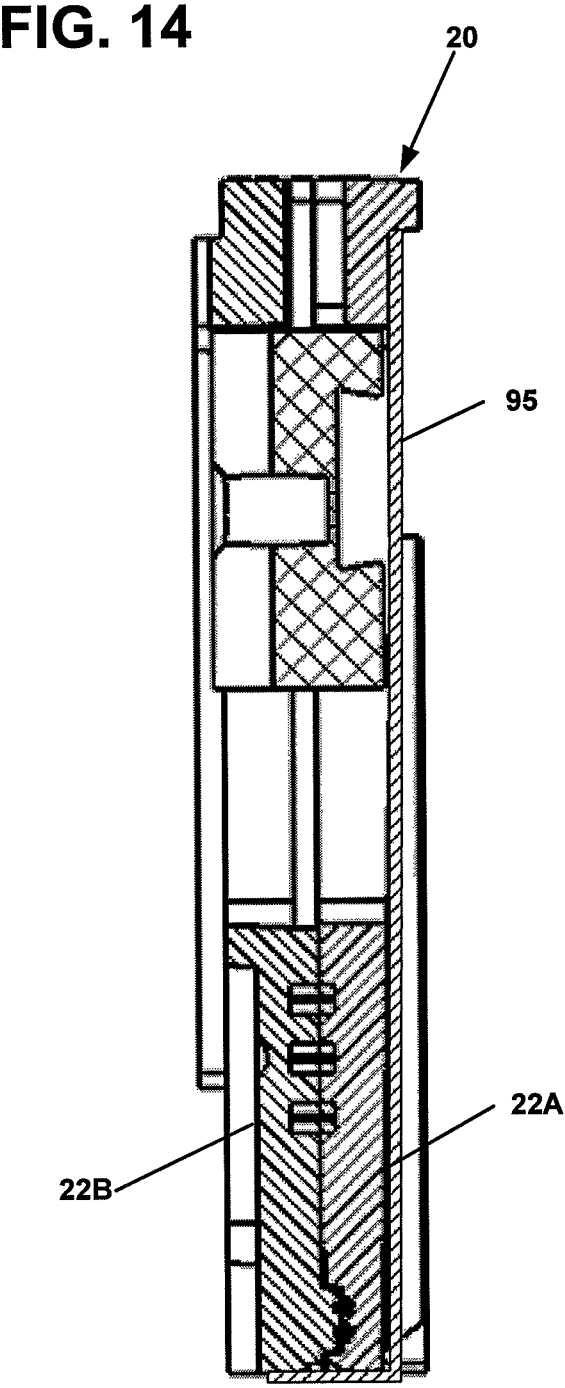
FIG. 14 shows the sensor module of FIG. 1 with a sealing member sealing applied to a sampling end and one of the major sides of the sensor housing.

In certain embodiments, the analysis zone of each module 20 can be sealed to limit the air exposure of the sensing chemistry provided on the working electrode. In one embodiment, the analysis zone can be sealed by a sealing member (e.g., a polymeric tape, a metal tape such as a foil tape, a sealing layer, a sealing sheet, a sealing media, etc.) affixed (e.g., adhesively bonded) to an outer surface of the main housing. In one embodiment, the sealing member is affixed to the sampling end 32 of the housing 22 such that the end of the passage 42 is covered and sealed and the sealing member is also affixed to one or both of the major sides of the housing to seal such sides. In certain embodiments, structures can be provided for automatically removing or piercing at least portions of the sealing member when it is desired to use a given sensor module. For example, the actuator 123 can penetrate/break a portion of the sealing member covering a major side of the sensor module so as to allow the actuator to connect to the slide member 38. Also, during use, the sampling end 32 of the main housing 22 with the sealing member attached thereto can be pressed against a person's skin at a desired sampling site. The skin piercing member 36 can then be extended so as to pierce through the sealing member and puncture the person's skin. The puncture wound aligns with the pierced hole in the sealing member so that blood can flow from the puncture wound through the hole in the sealing member to fill the funnel structure 72. From the funnel structure 72, the blood flows through the passage 42 to analysis zone 23. At FIG. 14, an example sealing member 95 is shown affixed to the sampling end 32 of the main housing 22 and to a major side of the housing 22 defined by the first piece 22A of the housing 22.

The invention claimed is:

1. A sensor module comprising:
a main housing defining an analysis zone within the housing, the main housing having a sampling end;
a skin piercing member mounted within the main housing, the skin piercing member being movable relative to the main housing along a slide axis between a retracted position and an extended position;
first and second electrodes positioned at the analysis zone and extending in a direction perpendicular to the slide axis; and
a fluid sample flow passage that extends from the sampling end of the main housing to the analysis zone, the fluid sample flow passage including a funnel structure at the sampling end through which the skin piercing member extends when in the extended position and a passage extending from the funnel structure into the analysis zone, the funnel structure having a first width at the sampling end and a second width at an opposite end, the second width being smaller than the first width, the fluid sample flow passage also including capillary flow enhancing slots extending in a direction perpendicular to the first and second electrodes from the funnel structure first width at the sampling end to the funnel structure second width at the opposite end and the capillary flow enhancing slots extending laterally from opposite sides of the funnel structure first width to define a width of the sampling end, wherein the width of the sampling end is greater than the first width of the funnel structure.

2. The sensor module of claim 1, wherein the analysis zone is sealed to limit a degree to which the sensing chemistry is exposed to air.

3. The sensor module of claim 2, further comprising a sealing member affixed to the sampling end of the main housing which covers the fluid sample flow passage, wherein the skin piercing member pierces the sealing member when the skin piercing member is moved to the extended position.

4. The sensor module of claim 1, wherein the first and second electrodes are elongated and have wetted lengths, and wherein the width of the fluid sample flow passage defined by the capillary flow enhancing slots is at least 75 percent as long as each of the wetted lengths, wherein the sample fluid flow passage continuously maintains the width as the fluid sample flow passage extends from the sampling end of the main housing to the analysis zone.

5. The sensor module of claim 4, wherein the first and second electrodes comprise conductive fibers.

6. The sensor module of claim 1, wherein the capillary flow enhancing slots have a first open end at the sampling end, and a second at least partially open end adjacent to the first electrode positioned at the analysis zone, the width of the capillary flow enhancing slots being equal at the first open end and at the second at least partially open end.

7. The sensor module of claim 1, wherein the capillary flow enhancing slots are defined between generally parallel planar surfaces separated by a thickness of 0.002 to 0.004 inches.

8. The sensor module of claim 1, wherein the first and second electrodes are positioned substantially parallel to each other and have a longitudinal axis extending in a substantially perpendicular direction across the fluid sample flow passage.

9. The sensor module of claim 4, wherein the width of the fluid sample flow passage defined by the capillary flow enhancing slots is at least 90 percent as long as each of the wetted lengths.

10. The sensor module of claim 1, wherein the skin piercing member passes through the fluid sample flow passage when in the extended position.

11. The sensor module of claim 1, wherein the skin piercing member includes a base end anchored to a slide member that is mounted within an elongated slot defined by the main housing, wherein the slide member is mounted to slide along a length of the slot within the main housing.

* * * * *